United States Patent [19]

Sartori et al.

[11] Patent Number: 5,180,496
[45] Date of Patent: Jan. 19, 1993

[54] UNSATURATED POLYESTERS AND CROSSLINKED MEMBRANES THEREFROM FOR AROMATICS/SATURATES SEPARATION

[75] Inventors: Guido Sartori; W. S. Winston Ho, both of Annandale; Robert E. Noone, Neshanic Station, all of N.J.

[73] Assignee: Exxon Research and Engineering Company, Florham Park, N.J.

[21] Appl. No.: 871,202

[22] Filed: Apr. 16, 1992

Related U.S. Application Data

[62] Division of Ser. No. 775,887, Oct. 11, 1991.

[51] Int. Cl.⁵ .............................................. B01D 61/00
[52] U.S. Cl. .................................... 210/654; 528/272; 528/274; 528/300; 528/302; 528/303; 528/306; 524/364; 210/640; 210/649; 585/818; 585/819
[58] Field of Search ............... 528/272, 274, 300, 302, 528/303, 306; 524/364; 210/640, 649, 654; 585/818, 819

[56] References Cited

U.S. PATENT DOCUMENTS

| | | | |
|---|---|---|---|
| 2,930,754 | 3/1960 | Stuckey | 585/819 |
| 2,958,656 | 11/1960 | Stuckey | 585/819 |
| 3,370,102 | 2/1968 | Carpenter et al. | 585/819 |
| 4,115,465 | 9/1978 | Elfert et al. | 585/819 |
| 4,342,859 | 8/1982 | Harada et al. | 528/64 |
| 4,944,880 | 7/1990 | Ho et al. | 210/640 |
| 4,946,594 | 7/1990 | Ho et al. | 210/640 |
| 4,976,868 | 12/1990 | Sartori et al. | 210/640 |
| 4,990,275 | 2/1991 | Ho et al. | 252/62.3 |
| 4,997,906 | 3/1991 | Thaler et al. | 528/272 |
| 5,012,035 | 4/1991 | Sartori et al. | 585/819 |
| 5,012,036 | 4/1991 | Sartori et al. | 585/819 |
| 5,019,666 | 5/1991 | Sartori et al. | 585/819 |

*Primary Examiner*—John Kight, III
*Assistant Examiner*—Sam A. Acquah
*Attorney, Agent, or Firm*—Ronald D. Hantman

[57] ABSTRACT

The present invention describes a method for the synthesis of unsaturated aliphatic polyesters, their crosslinking by thermal treatment and the use of the corresponding crosslinked membranes to separate aromatics from saturates.

4 Claims, No Drawings

UNSATURATED POLYESTERS AND CROSSLINKED MEMBRANES THEREFROM FOR AROMATICS/SATURATES SEPARATION

This is a division of application Ser. No. 775,887, filed Oct. 11, 1991.

BACKGROUND

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type i.e., aromatic, unsaturated, saturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g. aromatic and/or olefinic from gasoline boiling range mixtures by the selective permeation of the aromatic through certain nonporous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation. U.S. Pat. No. 5,028,685 discloses halogenated polyurethanes and membranes therefrom for separating aromatics from saturates.

U.S. Pat. Nos. 4,944,880 and 4,990,275 describe polyimide/aliphatic polyester copolymers and membranes therefrom for the separation of aromatics from saturates. U.S. Pat. Nos. 4,946,594 and 4,997,906 describe crosslinked copolymers of aliphatic polyester diols and dianhydrides and membranes therefrom for the separation of aromatics from saturates.

U.S. Pat. No. 4,976,868 covers the use of polyester membranes (e.g., polyethylene terephthalate, polybutylene terephthalate, and polyethylene terephthalate/-cyclohexane-dimethanol terephthalate) for aromatics/-saturates separation. U.S. Pat. Nos. 5,012,036, 5,012,035, and 5,019,666 teach the use of polyarylate, polyphthalatecarbonate, and non-porous polycarbonate membranes, respectively, to separate aromatics from saturates.

The present invention describes a process for the preparation of unsaturated aliphatic polyesters by reaction of oligomeric polyester diols with unsaturated diacid chlorides. The invention also describes a method to crosslink unsaturated aliphatic polyesters by thermal treatment. In addition, the invention describes the use of crosslinked membranes prepared from unsaturated aliphatic polyesters for the separation of aromatics from saturates.

Compared to distillation, membrane permeation can lead to considerable energy savings. A membrane can separate a mixture of aromatics and saturates, e.g., a heavy catalytic naphtha, into a high-octane, mainly aromatic permeate and a high-cetane, mainly saturated retentate. Both permeate and retentate are more valuable than the starting heavy catalytic naphtha.

SUMMARY OF THE INVENTION

The present invention is a method for the synthesis of unsaturated aliphatic polyesters by reaction of unsaturated diacid chlorides with oligomeric polyester diols. The invention also covers a method to thermally crosslink membranes prepared from the above polyesters and the use of the crosslinked membranes to separate aromatics from saturates.

DESCRIPTION OF THE PREFERRED EMBODIMENT

In the present invention, unsaturated polyesters are synthesized, membranes prepared from them are cast and thermally crosslinked and the resulting crosslinked membranes are used to separate aromatics from non-aromatics into an aromatic-enriched fraction and a non-aromatic-enriched fraction.

The membranes are useful for the separation of aromatics from saturates in petroleum and chemical streams, and have been found to be particularly useful for the separation of large substituted aromatics from saturates as are encountered in heavy catalytic naphtha streams. Other streams which are also suitable feed streams for aromatics/saturates separation are intermediate catalytic naphtha streams boiling at 93° C.–160° C., light aromatics content streams boiling in the 40° C.–150° C. range, light catalytic cycle oil boiling in the 200° C.–345° C. range as well as streams in chemical plants which contain recoverable quantities of benzene, toluene, xylenes (BTX) or other aromatics in combination with saturates. The separation techniques which may successfully employ the membranes of the resent invention include perstraction and pervaporation.

Perstraction involves the selective dissolution of particular components contained in a mixture into the membrane, the diffusion of those components through the membrane and the removal of the diffused components from the downstream side of the membrane by the use of a liquid sweep stream. In the perstractive separation of aromatics from saturates in petroleum or chemical streams, the aromatic molecules present in the feed stream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction and relies in vacuum on the permeate side to evaporate the permeate from the surface of the membrane and maintain the concentration gradient driving force which drives the separation process. As in perstraction, the aromatic molecules present in the feed dissolve into the membrane film, migrate through said film and emerge on the permeate side under the influence of a concentration gradient. Pervaporation separation of aromatics from saturates can be performed at a temperature of about 25° C. for the separation of benzene from hexane but for separation of heavier aromatic/saturate mixtures, such as heavy catalytic naphtha, higher temperatures of at least 80° C. and higher, preferably at least 100° C. and higher, more preferably at least 120° C. and higher should be used. Temperatures of about 200° C. have been successfully used with crosslinked membranes, prepared from unsaturated polyesters of the present invention, the maximum upper limit being that temperature at which the membrane is physically damaged. Vacuum on the order of 1-50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

When the membrane is used in a hollow fiber configuration with the feed introduced on the exterior side of the fiber, the sweep liquid flows on the inside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

The present invention shows that oligomeric polyester diols can be reacted with unsaturated diacid chlorides to give high-molecular-weight unsaturated polyesters. The oligomeric polyester diol can be, e.g., a polyethyleneadipatediol, a polyethylenesuccinatediol, a polymalonatediol, a polyoxalatediol, or a polyglutaratediol of molecular weight between about 500 and 5000. The unsaturated diacid chloride can be aliphatic or cycloaliphatic, such as maleyl chloride, fumaryl chloride, itaconyl chloride, mesaconyl chloride or 5-norbornene-2,3-dicarbonyl chloride. Mixtures of oligomeric polyester diols and/or mixtures of unsaturated diacid chlorides can also be used. A tertiary amine, e.g., triethylamine, triethylene diamine, or pyridine, can be used to trap the hydrochloric acid formed during the reaction. In addition, a solvent, e.g., a chorinated aliphatic hydrocarbon such as chloroform, 1,2-dichloroethane or methylene chloride, or an aromatic such as benzene, toluene, xylene or chlorobenzene, can be used during the reaction or added at the end to achieve the desired fluidity. Membranes are cast, the solvent evaporated and then the membranes are heated to crosslink them. Then the membranes are washed with water to remove the tertiary amine hydrochloride and then dried in an oven.

The membranes are used to separate aromatics from saturates in a pervaporation apparatus. The pervaporation apparatus is a cell, separated into two compartments by a porous metal plate, on which the membrane is supported. During a pervaporation experiment the aromatics/saturates mixture is circulated through the upper compartment at the desired temperature. The lower compartment is kept at reduced pressure. The permeate is collected in a trap cooled with dry ice-acetone or dry ice-isopropanol and periodically analyzed by gas chromatography. The feed contains 20 wt. % isooctane, 10% toluene, 30% n-octane and 40% p-xylene. The following examples illustrate the invention.

EXAMPLE 1

The reaction apparatus was a 150 ml glass vessel, equipped with stirrer, thermometer and gas-inlet tube and kept under nitrogen. 15 g of dry polyethyleneadipatediol of average molecular weight 500 (30 mmoles), 6.06 g of triethylamine (60 mmoles), and 60 g of anhydrous chloroform were put into the reactor. When everything was dissolved, the reaction vessel was cooled by immersion in ice water, then 4.59 g of fumaryl chloride (30 mmoles) dissolved in 15 g anhydrous chloroform was added over a period of about 20 minutes, without allowing the temperature to exceed 19° C. After 1 hour and 40 minutes the reaction was stopped by adding 1.5 ml of methanol.

The reactor was then heated gently until about ½ the solvent was driven off to obtain a castable solution. After cooling, a membrane was cast on Gore-tex (porous teflon) and covered with another Gore-tex sheet.

The membrane was subjected to the following thermal cycle in a nitrogen-purged oven:

| Temperature (°C.) | Hours |
| --- | --- |
| 100 | 15 |
| 150 | 15 |
| 200 | 15 |
| 250 | 7 |

During the thermal treatment the membrane became less tacky. At the end it was rubbery, insoluble in chloroform, i.e., crosslinked, and not brittle. The membrane was immersed in water overnight to remove triethylamine hydrochloride, dried in vacuo overnight, then at 100° C. at atmospheric pressure for five hours.

The above membrane was tested in a pervaporation cell, in which the feed consisted of 2% (by weight)

thiophene, 10% toluene, 33% p-xylene, 3% benzothiophene, 20% isooctane and 32% n-octane.

The following table gives the pervaporation results.

| Temperature (°C.) | Toluene/n-Octane Separation Factor | Normalized Flux (kg · μM/M² · D) |
|---|---|---|
| 150 | 4.9 | 6,380 |
| 170 | 4.3 | 8,970 |
| 190 | 3.7 | 10,000 |

Another piece of membrane was heated at 250° C. for an additional 15 hours. It was tested in a different permeator, in which the feed contained equal amounts of toluene and n-octane. The following table gives the results.

| Temperature (°C.) | Toluene/n-Octane Separation Factor | Normalized Flux (kg · μM/M² · D) |
|---|---|---|
| 150 | 4.9 | 4,510 |
| 170 | 4.5 | 6,290 |
| 190 | 4.2 | 9,260 |
| 205 | 4.2 | 11,190 |
| 230 | 4.1 | 15,010 |

EXAMPLE 2

The reaction apparatus was the same as described in Example 1.

15 g of dry polyethyleneadipatediol, molecular weight=500, corresponding to 30 mmoles, was put into the reactor with 6.06 g of triethylamine (60 mmoles) and 60 g of anhydrous chloroform. The temperature was brought to below 20° C. by immersing the reactor in ice-water. When everything was dissolved, 6.6 g of 5-norbornene-2,3-dicarbonyl chloride (30 mmoles), dissolved in 15 ml of anhydrous chloroform, was added slowly, making sure that the temperature did not exceed 20° C.

After about an hour the solution became viscous enough to cast. After centrifuging ad discarding some solid precipitate floating on top, three membranes were cast on Gore-tex (porous teflon) sheets. Two membranes were placed on top of each other, i.e., with the Gore-tex sheets facing outside. Then the "sandwiched" membrane so obtained was put into a nitrogen-swept over and heated at 100° C., 150° C. and 200° C., each for 15 hours. Then the membrane was washed with water overnight to remove triethylamine hydrochloride, then dried in a vacuum oven at 100° C. overnight. Two pieces were further heated at 250° C., one for 7.5 hours, the other for 15 hours. The piece heated at 250° C. for 7.5 hours was evaluated in a pervaporator by the use of a feed consisting of 10% toluene (by weight), 40% p-xylene, 20% isooctane and 30% n-octane. The following table gives the results.

| Temperature (°C.) | Toluene/n-Octane Separation Factor | Normalized Flux (kg · μM/M² · D) |
|---|---|---|
| 150 | 6.1 | 2,410 |
| 170 | 5.7 | 3,000 |
| 190 | 5.1 | 4,240 |
| 210 | 4.6 | 5,360 |

The membrane heated at 250° C. for 15 hours was evaluated in a different permeator by the use of a feed consisting of equal amounts of toluene and n-octane. The following table gives the results.

| Temperature (°C.) | Toluene/n-Octane Separation Factor | Normalized Flux (kg · μM/M² · D) |
|---|---|---|
| 150 | 5.2 | 1,414 |
| 170 | 5.1 | 2,090 |

What is claimed is:

1. A method for separating mixtures of aromatics and non-aromatics into aromatic-enriched and non-aromatic-enriched streams comprising:
   a) contacting said aromatics/non-aromatics mixture with one side of a crosslinked membrane prepared by reacting an oligomeric polyester diol with an unsaturated diacid chloride, and
   b) selectively permeating the aromatic component of the mixture through the membrane.

2. The method of claim 1 wherein the polyester diol is selected from the group consisting of polyethyleneadipatediol, polyethylenesuccinatediol, polymalonatediol, polyoxalatediol, polyglutaratediol, and mixtures thereof.

3. The method of claim 1 wherein the unsaturated diacid chloride is selected from the group consisting of maleyl chloride, fumaryl chloride, itaconyl chloride, mesaconyl chloride, 5-norbornene-2,3-dicarbonyl chloride, and mixtures thereof.

4. The method of claim 1 wherein the aromatics/non-aromatics mixture is selected from heavy catalytic naphtha streams, intermediate catalytic naphtha streams, light aromatics streams boiling in the 40°–150° C. range, and light catalytic cycle oils boiling in the 200° C.–345° C. range.

* * * * *